United States Patent [19]

Faucher

[11] Patent Number: 5,353,809
[45] Date of Patent: Oct. 11, 1994

[54] HOSPITAL BARCCHIAL SUPPORT

[76] Inventor: Germain Faucher, 26 Rue Thibault, Lévis (Que), Canada, G6V 2J7

[21] Appl. No.: 46,192

[22] Filed: Apr. 12, 1993

[51] Int. Cl.⁵ .......................................... A61G 13/12
[52] U.S. Cl. .................... 128/845; 128/878; 5/646
[58] Field of Search .............. 128/845, 877, 878, 882, 128/879, 881; 378/208; 5/646, 623, 647, 632; 428/905, 907, 118

[56] References Cited

U.S. PATENT DOCUMENTS

| | | | |
|---|---|---|---|
| 2,507,172 | 5/1950 | Haclerio | 5/623 |
| 2,743,975 | 5/1956 | Stiefoater | 5/647 |
| 2,766,463 | 10/1956 | Bendersky | 5/623 |
| 2,978,713 | 4/1961 | Scalzitti et al. | 128/882 |
| 3,020,909 | 2/1962 | Stevens | 5/623 |
| 4,210,317 | 7/1980 | Spanu et al. | 5/647 |
| 4,698,837 | 10/1987 | Van Steenburg | 5/623 |
| 4,730,801 | 3/1988 | Cloward | 5/646 |
| 4,807,618 | 2/1989 | Auchinleck et al. | 128/878 |
| 4,836,523 | 6/1989 | Englander | 5/647 |
| 4,964,400 | 10/1990 | Laico et al. | 128/878 |
| 5,000,168 | 3/1991 | Lipson | 128/845 |
| 5,136,743 | 8/1992 | Pirela-Cruz | 378/208 |

FOREIGN PATENT DOCUMENTS

| | | | |
|---|---|---|---|
| 1049996 | 3/1979 | Canada | 248/47 |
| 1252144 | 4/1989 | Canada | 311/4 |
| 4022836 | 1/1992 | Fed. Rep. of Germany | 128/845 |
| 2156225 | 10/1985 | United Kingdom | 128/878 |

OTHER PUBLICATIONS

Lile Inter. CL 2.
Dyer Inter. CL 4.
Disclosure Document Mar. 11 and Apr. 2, 1993.
Loose Photographs.

*Primary Examiner*—Robert A. Hafer
*Assistant Examiner*—Michael O'Neill

[57] ABSTRACT

There is provided a support for the arms of a patient undergoing x-ray analysis or treatments requiring raising an arm above one's head and maintaining the arm in that position for any length of time. The use of the apparatus is comfortable and reduces stess. A header is adapted to be secured to the head end of the table supporting the patient. A pair of posts are fixed to and upstand from the header and each carries a horizontally disposed elongated arm rest in cantilever fashion with the post protruding above the arm rest to form a hand grip to be grasped by the patient lying on his back on the table. Each arm rest has an arm restraining upstanding flange on its external side. The level and angular position of each arm rest can be adjusted. Each arm rest can be installed below the table when the patient is to be treated in prone condition.

4 Claims, 5 Drawing Sheets

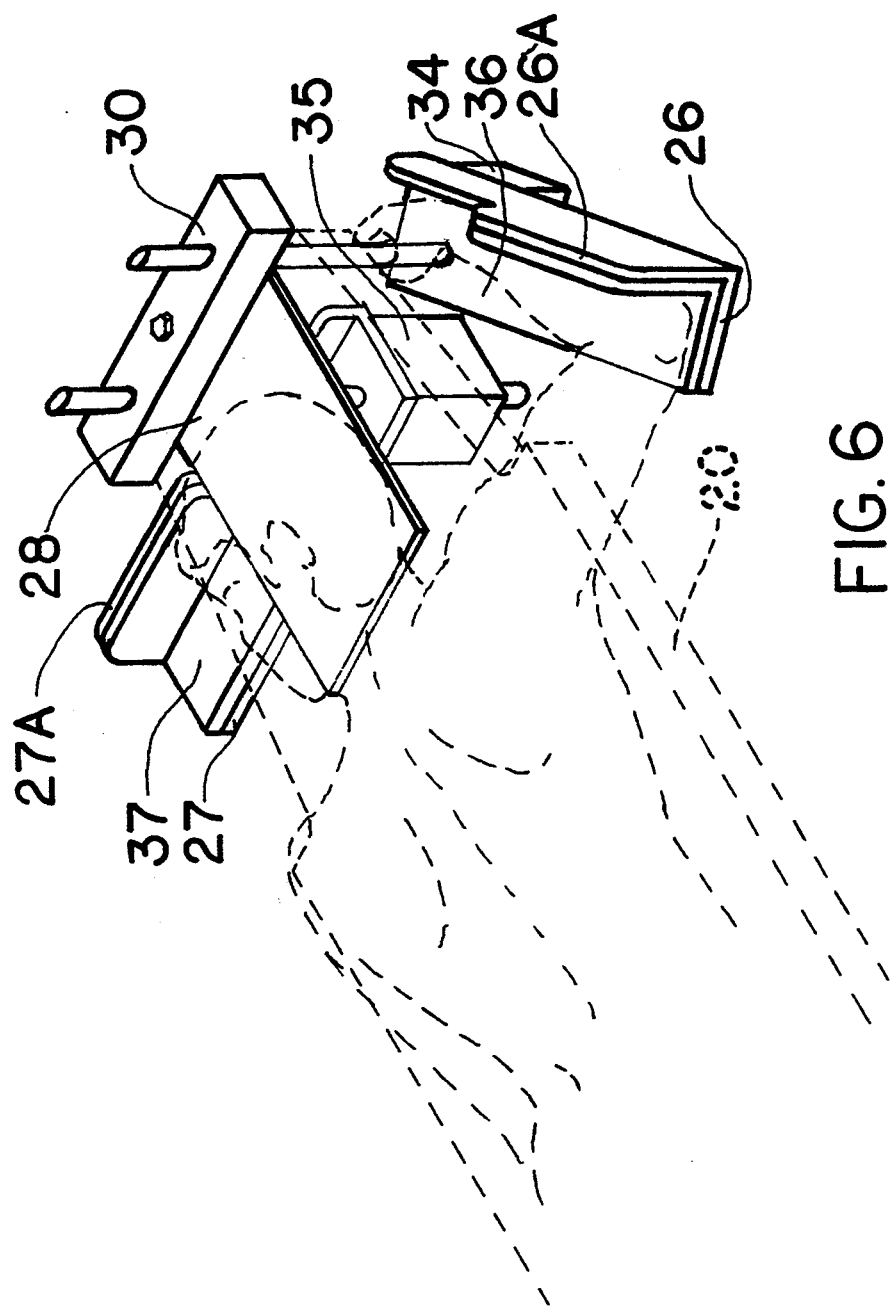

HOSPITAL BARCCHIAL SUPPORT

BACKGROUND

1. Field of the Invention

This invention is related to the positioning of two arms above the head for exposure in X-ray and nuclear medicine and for treatment in radio-oncology.

2. Description of Prior Art

The known methods of positioning a patient's two arms involve moving the x-ray table to a position sensibly perpendicular to the location of the tip of the x-ray generating equipment. The positioning of the arm for underarm picture taking is done by stretching the arm and trying to immobilize the patient during the x-ray generation process, resulting in much discomfort. The use of supports installed externally to the table may cause undue strain, should the table be rotated significantly.

In the prior art Patent CAN 1,049,996 Lile, March 1979 discloses an extremity holder for mounting on an operating table but dependent upon the presence of apertures in the end of the table as well as the presence of a rail as part of a table.

Another piece of prior art Can 1,252,144 Dyer, April 1989, discloses a hand grip for keeping the arms above the head and an attachment to the table by means of a pelvic belt for resisting traction but here again the system necessitates the adapting of the table to the needs of traction by making the table slidably mounted, such system being too complex for day to day X-ray analysis application and for eventual use on an emergency stretcher.

OBJECTS OF THE INVENTION

An object of the present invention is to provide an improved bracchial support.

Another objective of the new piece of equipment is to provide support for a patient's arm limb placed either above or below the table.

In accordance with another aspect of the present invention there is provided a support which utilizes the weight of the person's head or shoulders to secure the support onto the table.

SUMMARY OF THE INVENTION

In accordance with the invention there is provided a bracchial support for supporting a patient's arm beyond his head while lying on a table, comprising a header, means to fix the header to the table, a pair of posts upstanding from the header and spaced from each transversely of the table, the posts having an upper end portion forming a hand grip, a pair of elongated arm rests, each defining an external and an internal side, each arm rest extending from one of said posts in cantilever fashion below the hand grip and above the header and towards the other end of the table, the external side of each arm rest being remote from the external side of the other arm rest, an arm restraining flange secured to and upstanding from the arm rest along the external side thereof, clamping means carried by the arm rests and engageable with the posts to adjustably clamp the arm rests in a horizontally rotated position about the posts and at a desired level between the hand grips and the header. Preferably, the header is fixed to one end of a pad which is adapted to be maintained over the table under the head of the patient with the header located beyond the patient's head. Preferably, the posts are of circular cross-section and the header has circular holes through which the posts are rotatably inserted and the clamping means are carried by the header to clamp the posts to the header. Preferably, the holes are through bores and open below the pad and the posts can be inserted into the holes from below the header, there being further provided second clamping means carried by the arm rests whereby the arm rests can be adjustably clamped along the posts at an adjustable level below the header and they can be clamped in a rotated position along the posts so as to support the arms of the patient lying on the table in prone position. Preferably the pad incorporates a spring blade which is fixed to the outer ends of the transversely extending header and a biasing screw is screwed within the center portion of the header and is applied against the center of the pad to adjust the transverse curvature of the pad to fit a concave table head extension.

DRAWING FIGURES

The above mentioned and other advantages of the invention will better be understood in reference to the following description and drawings in which:

FIG. 6 is a perspective view of the arm rest positionned below an examination table appearing in dotted line.

DESCRIPTION

Figure 1:
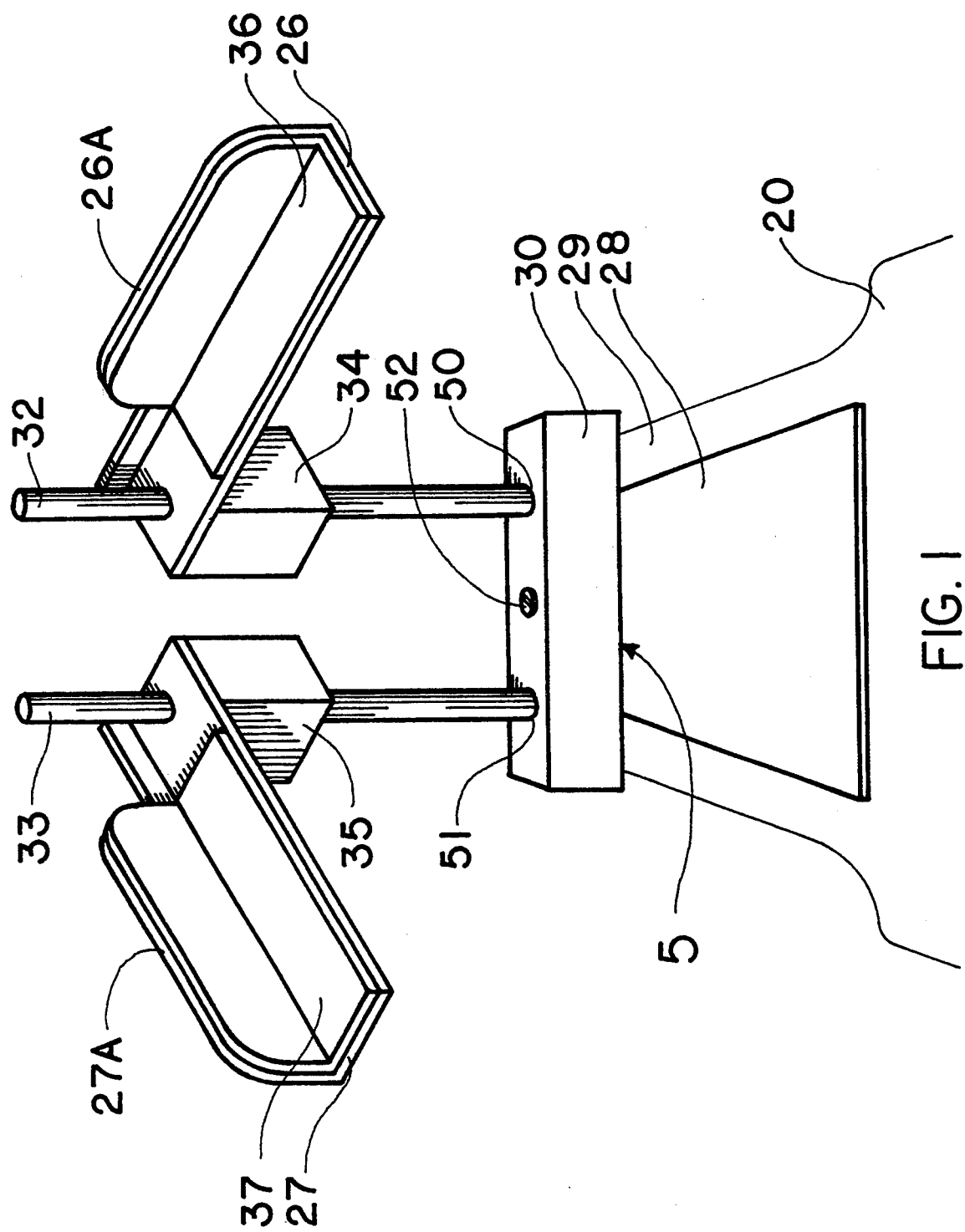
FIG. 1 is a perspective view of the bracchial support.
Figure 2:
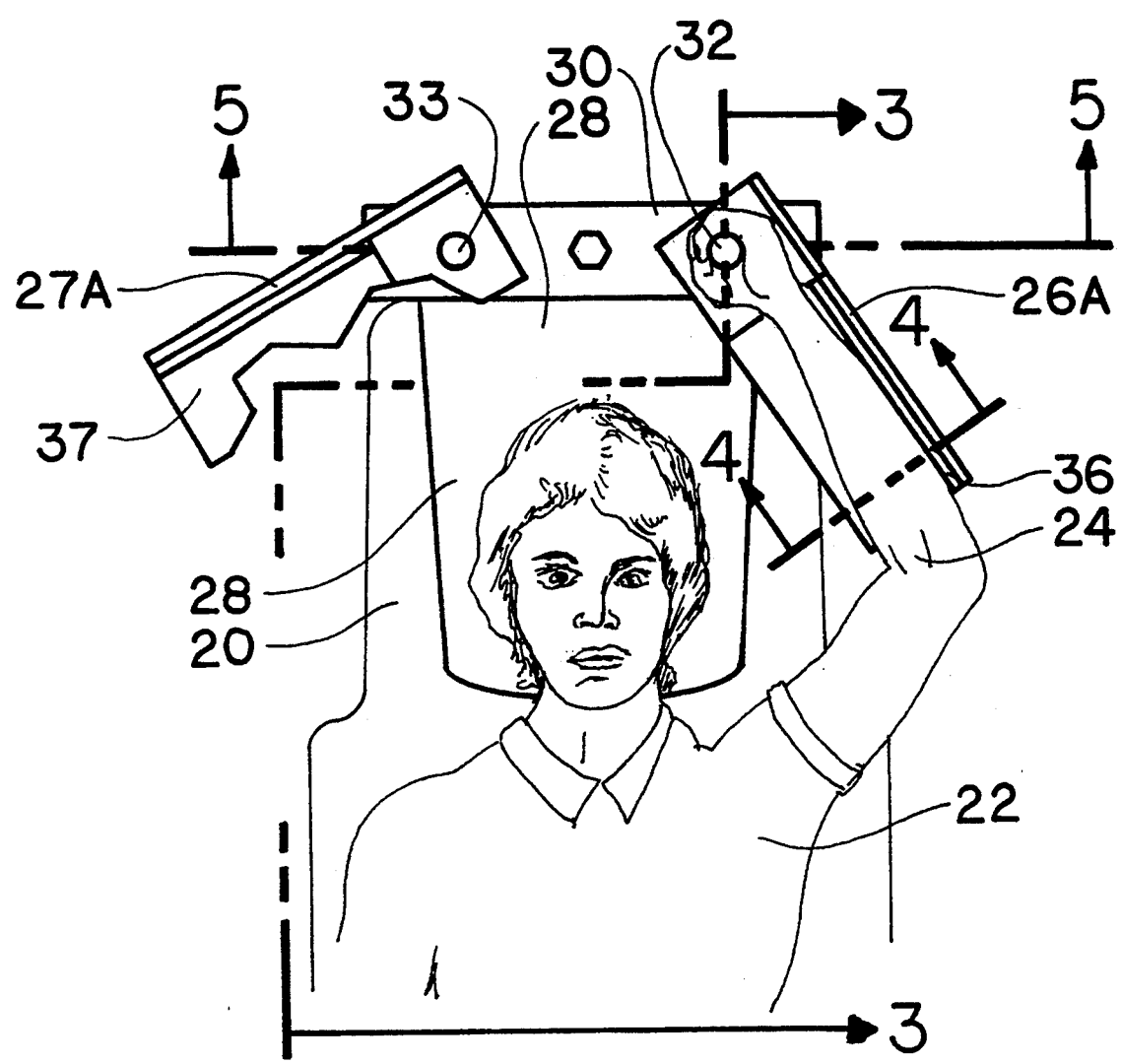
FIG. 2 is a top view of the same, one arm rest being partially cut away to show underlying parts.

Referring to FIG. 1, there is illustrated a table 20 and a patient 22..FIG. 2..laying on his back on the table. The person's left hand 24 is laying on arm rest 26. On the examination table 20 is mounted a thin support pad 28 which extends beyond the table end 29 into a header 30 to which the thin pad 28 is attached. Pad 28 is maintained on table 29 at least in part under the weight of the patient's head. The header 30 carries two vertical posts 32 and 33 of circular cross-section, one on the right side facing the table head end from the back and one on the left side. The posts 32, 33 are mobile..FIG. 1..with respect to the header 30, for 360 degree rotation and vertically. Arm rests 26, 27 are carried in cantilever fashion by the posts 32, 33 respectively. The posts extend sufficiently above the arm rests 26, 27 to form a hand grip to be grabbed by the patient's hands. Arm rests 26, 27 are elongated boards which are fixed at one end to right and left blocks 34 and 35, respectively. Each block 34, 35 has a through bore 40 through which a post extends. Screw means 38..FIG. 3..carried by each block 34, 35 clamps the arm rests 26, 27 to the posts 32, 33. Each posts 32, 33 passes through a through bore 50, 51 made in header 30 and through a registering hole 46 made in pad 38. A screw 44 clamps posts 32, 33 to header 30.

Header 30 is preferably a 2"×2" block, 8" long and holes 50, 51 are located at the ends of the header 30. Preferably, posts 32, 33 are 1" diameter rods, 12" long. The blocks 34 and 35 have a cubic shape with a central opening 40 of 1" diameter for a sliding fit of the rods 32 and 33. Clamping screw 38 clamps each block on the rod at the desired height and desired angle.

Figure 4:
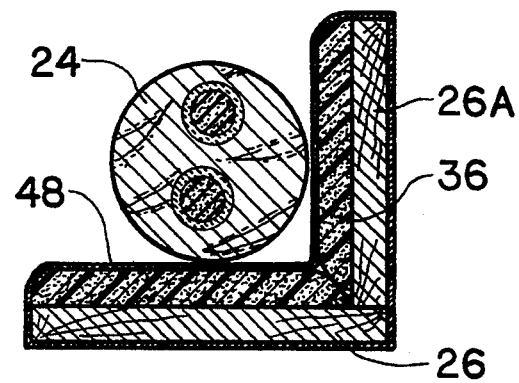
FIG. 4 is a section along line 4—4 of FIG. 3.

Each arm rest 26, 27 has an upstanding arm restraining flange 26a, 27a along its external side. Each arm rest 26, 27 is covered by a liner 36 preferably 7" long. The liner is preferably made of foam for comfort and covered by a leather or vinyl sheet 48..FIG. 4.

Figure 3:
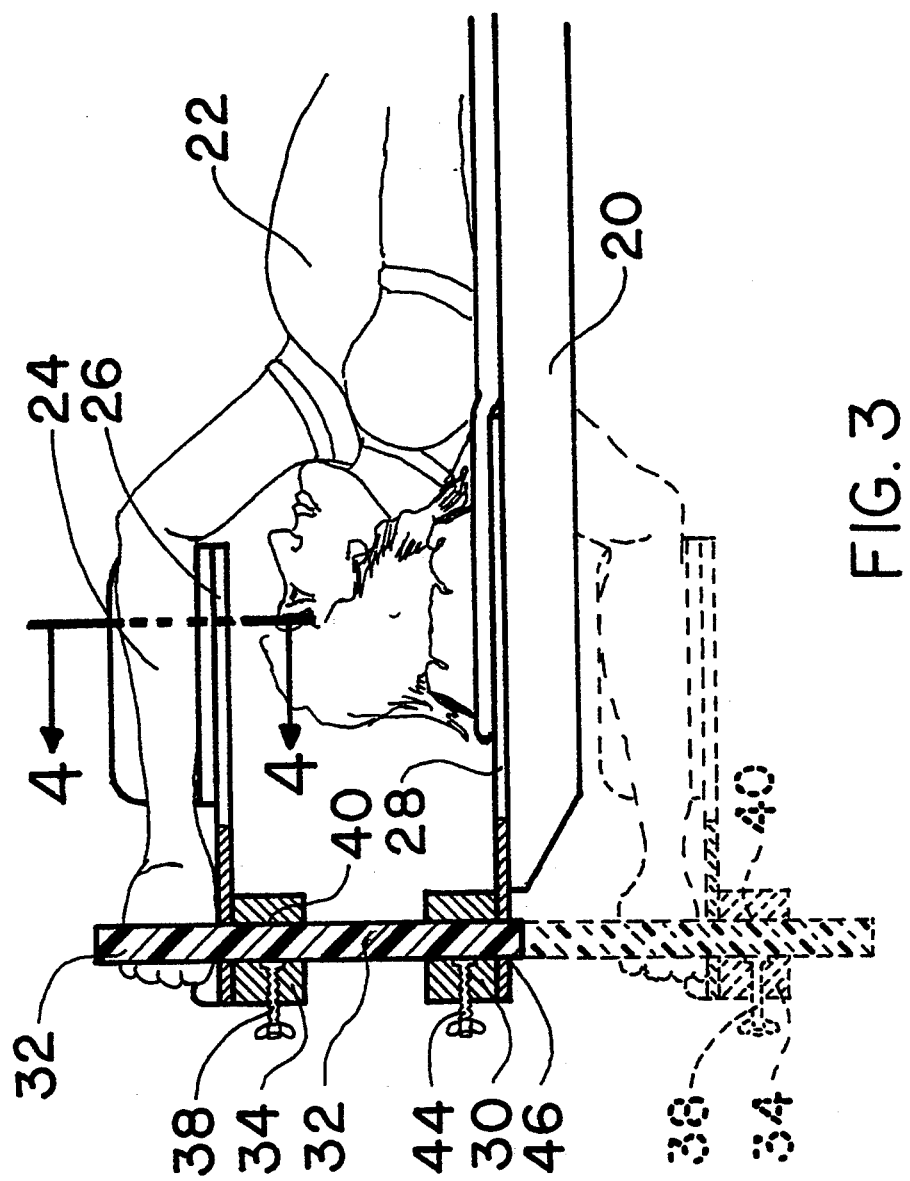
FIG. 3 is a side view thereof with alternative position in dotted line.

The arm rests 26, 27 can be adjustably disposed underneath the header 30 as shown in dotted line in FIG. 3 and also in FIG. 6, so as to hold the arms of a patient lying on the table in prone position. The two posts 32 and 33 are inserted within the header 30 through the through bores 50, 51 so as to extend underneath said header and the arm rests and the holding blocks 34 and 35 of the arm rests 26, 27 are fixed by the screw 38 to the posts 32, 33 in adjusted angular rotated position and at an adjustable level.

Figure 5:
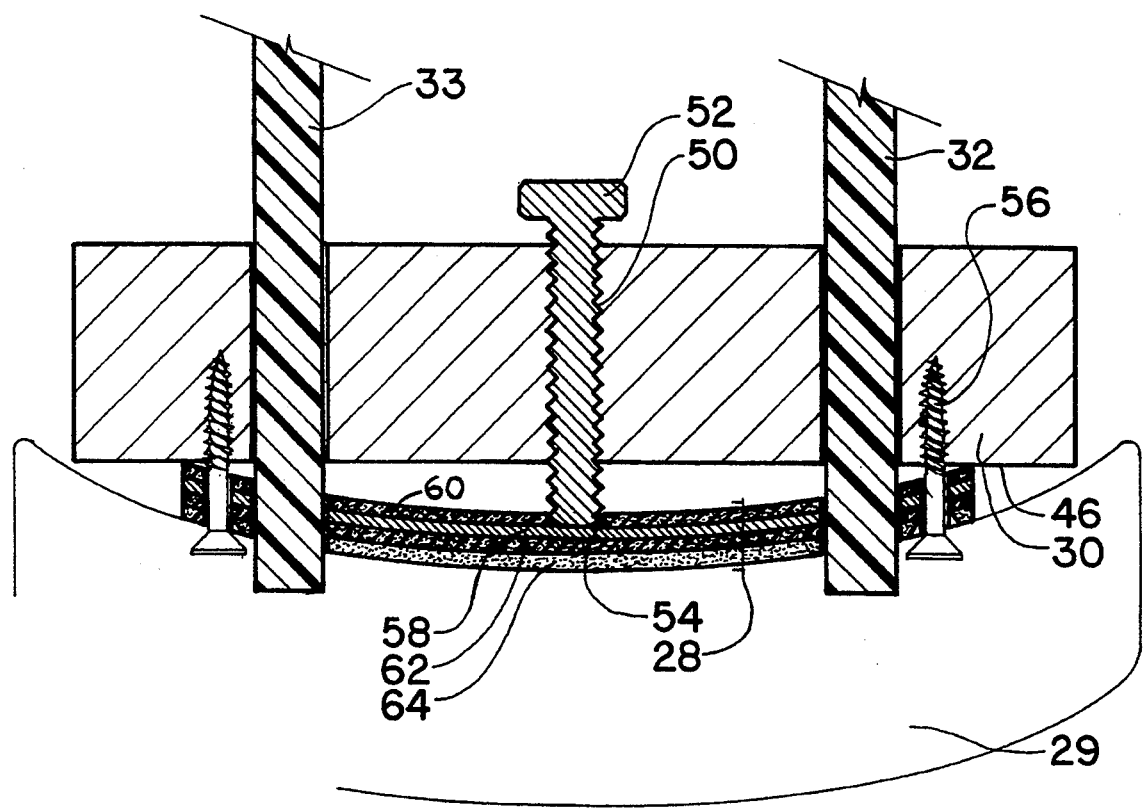
FIG. 5 is a section along line 5—5 of FIG. 1.

The table head extension 29 of an X-Ray table often has a slightly concave cross-section such as shown in FIG. 5. To conform pad 28 to this shape, a biasing screw 50 is threaded through the center portion of header 30 and has a head 52 and a pushing tip 54. To the bottom face 46 of the ends of block 30 is fixed the thin pad 28 by screws 56. Biasing screw 50 serves to adjustably bias the center of pad 28 away from header 30.

Pad 28 includes a metal leaf spring type blade 58 which is covered by rubber membranes 60 and 62 on its inner and other side respectively. Membrane 62 is in turn covered by an adhesive layer 64, to removably adhere the curved pad 28 to the table head extension 29.

A reduced scale version of the bracchial support of the invention can be made, for instance, for infants and for paralyzed arms requiring fastening of the arm to the support. However, it will be understood that other embodiments and variations of the one described are possible within the scope of the invention which is limited only by the scope of the appended claims.

I claim:

1. A brachial support for supporting a patient's arms beyond his head while lying on a table, comprising a header, means to fix said header to one end of said table, a pair of posts upstanding from said header and spaced from each other transversely of said table, said posts having an upper end portion forming a hand grip, a pair of elongated arm rests, each defining an external and an internal side, each arm rest extending from one of said posts in cantilever fashion below said hand grip, above said header and towards the other end of said table, said external side of each arm rest being remote from the external side of the other arm rest, an arm restraining flange secured to and upstanding from said arm rest along said external side thereof, clamping means carried by said arm rests and engageable with said posts to adjustably clamp said arm rests in a horizontally rotated position about said posts and at a desired level between said hand grips and said header.

2. A brachial support as defined in claim 1 further including a pad, said header fixed to one end of said pad, said pad adapted to be maintained over said table under the head of a patient lying on said table with said header located beyond the patient's head.

3. A brachial support as defined in claim 2, wherein said header has circular holes and said posts are circular in cross-section and are rotatably and slidably inserted within said circular holes and said clamping means are carried by said header to clamp said posts to said header.

4. A brachial support as defined in claim 3, wherein said holes are throughbores and open below said pad and said posts can be clamped by a header clamping means into said holes and extend below said header, whereby said arm rests are clamped to said posts below said header to support the arms of a patient lying on a table in a prone position with the portions of said posts extending between said header and said arm rests serving as hand grips.

* * * * *